United States Patent [19]

Yamazaki et al.

[11] Patent Number: 4,949,727
[45] Date of Patent: Aug. 21, 1990

[54] PORTABLE PHYSICAL CHECKER

[75] Inventors: Iwao Yamazaki; Katsumi Sakamoto, both of Tokyo, Japan

[73] Assignee: Ya-man Ltd., Tokyo, Japan

[21] Appl. No.: 331,051

[22] Filed: Mar. 28, 1989

Related U.S. Application Data

[63] Continuation of Ser. No. 181,325, Apr. 13, 1988, abandoned.

[30] Foreign Application Priority Data

May 27, 1987 [JP] Japan .............................. 62-78756[U]

[51] Int. Cl.⁵ ................................................ A61B 5/05
[52] U.S. Cl. .................................................... 128/734
[58] Field of Search ........ 128/734, 693, 774, 670–671, 128/687–690

[56] References Cited

U.S. PATENT DOCUMENTS

| | | | |
|---|---|---|---|
| 2,763,935 | 9/1956 | Whaley et al. | 128/734 X |
| 3,320,946 | 5/1967 | Dethloff et al. | 128/734 |
| 3,870,034 | 3/1975 | James | 128/734 |
| 4,008,712 | 2/1977 | Nyboer | 128/734 |
| 4,178,916 | 12/1979 | McNamara | 128/734 |
| 4,365,637 | 12/1982 | Johnson | 128/734 |
| 4,367,752 | 1/1983 | Jimenez et al. | 128/689 |

FOREIGN PATENT DOCUMENTS 61-253451 5/1985 Japan .
62-169023 1/1986 Japan .

*Primary Examiner*—William E. Kamm
*Attorney, Agent, or Firm*—Kane, Dalsimer, Sullivan, Kurucz, Levy, Eisele and Richard

[57] ABSTRACT

A portable physical checker which is provided with a display part, a group of the function changing-over keys and ten-keys for data input on the surface of the unit case where is sufficiently thinner than dimensions of height and width thereof and has the electrodes for measuring inner body impedance at reverse side of the above unit case, the central processing unit processes according to the input from above electrodes based on the setting with the above function changing-over keys and keys for data input and also the memory unit for data storage.

1 Claim, 2 Drawing Sheets

FIG. 1
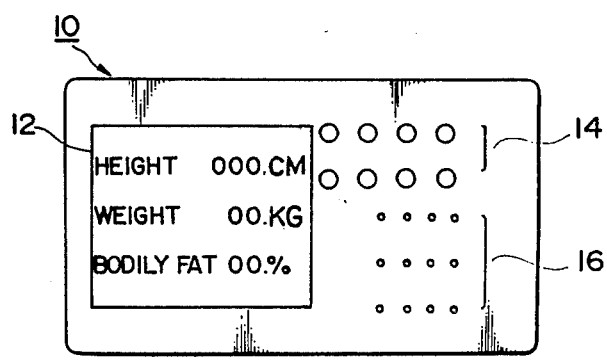
FIG. 2
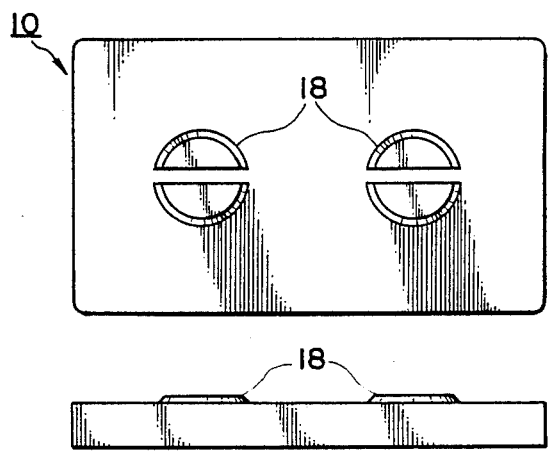
FIG. 4

PORTABLE PHYSICAL CHECKER

This application is a continuation of application Ser. No. 181325, filed Apr. 13, 1988 and now abandoned.

BACKGROUND OF THE INVENTION

1. Field of the Invention

This invention relates to a portable physical checker which makes a medical examination of a user according to the physical data and the measured data inputted by the keys.

2. Description of the Prior Art

If the proportion of fat contained in the inner body tissue system can be measured, it may be used as an effective standard to view beauty or health. However, the equipment which measures the amount body fat exactly has generally some faults that it is of a large size or it is complicated to use etc.

Gauges which measure with comparative ease the amount of fat in body tissue by the electrical resistance and impedance of the body are known.

As such a kind of the equipment, for example, what have been disclosed in the Japanese Patent Kokai No. Sho 61-253451 and No. Sho 62-169023 are known.

These fat gauges of bodily impedance measure the ratio of the bodily tissue components based on the electric resistance of the body and its impedance by attaching electrodes to the hand and foot of a person to be measured and drawing an exceedingly slight current.

In these equipments, error in the measurement is apt to occur depending on the measurement conditions and especially the status of the attached electrodes etc. so that they provide only poor data reliability.

In addition, these former equipments are set up at beauty salons or health centers etc., and many of them are presupposed to be operated by an experienced specialist.

Therefore, such equipment has not been suited for personal use or with ease at usual homes.

SUMMARY OF THE INVENTION

The purpose of this invention is to provide a portable physical checker of a card shape or another handheld shape, which can indicate or advise the grade of corpulency and the state of personal health based on the bodily fat component and other bodily data of a person to be measured.

The features of a portable physical checker in accordance with this invention includes a case and a display part, a group of the function changing-over keys and ten-keys for data input on the surface of its case where is significantly thinner than the dimensions of its height and width, and has electrodes for measuring bodily impedance at the reverse side of the case. The device also has a Central Processing Unit which processes according to the input from the above electrodes based on the setting with the above function changing-over keys and keys for data input and also has a Memory Unit for data storage.

According to the portable physical checker of this invention, measurement of the componental ratio of a person's bodily fat may be effected, and calculation required is effected by adding the basic datas inputted previously, e.g. sex distinction, age, height, and weight etc. In addition display of the proper calories to be taken corresponding to the measured quantity of bodily fat, a display of the held calories of the food taken practically and a display of the standard of proper meal contents with exercise quantity on the appointed day added, etc. may be effected.

The, the above physical checker can be used as an index for the maintenance and management of many conditions for a user's beauty or health and may be carried and possessed constantly with ease.

BRIEF DESCRIPTION OF THE DRAWINGS

The other features and asdvantages of this invention will be more clarified by the under-mentioned explanation corresponding to the appended drawings.

FIG. 1 is an appearance view of the surface of a portable physical checker according to this invention.

FIG. 2 is an appearance view of the reverse side of a portable physical checker according to this invention.

FIG. 3 is a block diagram indicating the fundamental structure of a portable physical checker according to this invention and FIG. 4 is a side view of the portable physical checker of this invention.

DETAILED DESCRIPTION OF PREFERRED EMBODIMENTS

Figure 3:
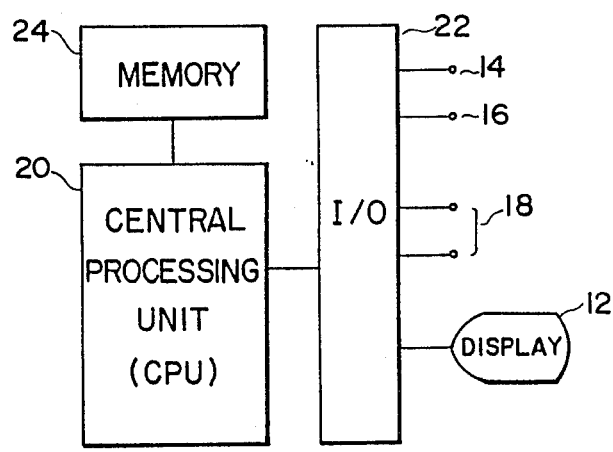

FIG. 1 shows a shape of the surface of the case 10 of a portable physical checker 10 in accordance with this invention. The case 10 is equipped with a displaying part 12, a group of function keys 14 and keys 16.

In the displaying part 12, a liquid crystal display and the other proper displaying elements may be used, and the displaying part displays the inputted data, the measured data, the result of calculation and the message to the user etc.

The group of function keys 14 is used for changing the function for the working of the portable physical checker and for the other uses.

For example, each mode of the inner body impedance measuring mode, body data inputting mode, calory matching meal displaying mode, consumed calory matching exercise displaying mode, calculating mode and takable calory displaying mode are used to indicate the desired action to the portable physical checker or to get the message by depressing the single key or complex keys.

The keys 16 are used to input data at the action mode which is selected by the group of function keys 14.

In the drawings there are 12 keys shown, the marker keys required for data input such as +, −, /, *, ', =, etc. in addition to the numbers from 0 to 9 are naturally contained.

FIG. 2 shows the shape of the reverse side and FIG. 4 shows the shape of the side of the portable physical checker according to this invention and two sets of electrodes 18 which are divided into two respectively are illustrated.

These electrodes 18 correspond to the input terminals of the circuit, which measure the electric resistance of the inner body and the impedance of the inner body by being touched to the left and right fingers respectively.

These electrodes are composed of electric conductors which slightly protrude from the surface of the unit case so as to be easy to touch by the fingers of the person to be measured.

As the principle and the manner relating to the electric resistance of inner body and the impedance of inner body in this case, the technique which is disclosed in the Japanese Patent Kokai No. Sho 62-169023 filed by the assignee of this application may be applied.

FIG. 3 is the block diagram showing the basic construction of the portable physical checker 10 according to this invention, and the central processing unit (CPU) 20 can effect inputting/outputting of the each factor shown in FIG. 1 and FIG. 2 through the inputting/outputting unit 22.

Also, to the central processing unit 20 is connected a memory unit 24, which can store not only the program for action but also the inputted data, the measured data and the required data of the calculated result etc.

It is decided depending upon the sort and the precision of the function desired as the portable physical checker, at what level the storage capacity of this memory unit is made.

According to the portable physical checker shown herein, after the electric resistance of the inner body and the impedance of the inner body measuring mode has been selected by means of the group of function keys 14, the electric resistance of the inner body and the impedance of the inner body may be measured by touching the left and right fingers to the electrodes 18 certainly.

Moreover, if the weight is inputted from the ten-keys 16 as the body data of the person, the ratio of the fat occupied in the bodily tissue is calculated by the central processing unit 20, and each of the data and the results of calculation are displayed at the display division 12.

Also, it can store the results of measurement and calculation at the memory unit 24, if necessary.

The memory unit 24 stores the data relating to the calories of representative foods and drinks, for example such as the flours meats, fishes, milk, vegetables and juice etc. as well as alcohols e.g. whiskey and beer, etc. and relating to the consumed calories by typical physical exercise, for example such as constitutional walk, jogging, running, playing tennis, playing golf or the like.

It can calculate, amend and display etc. corresponding to the selected function by applying such data properly.

As the examples of calculation and display, the proper quantity of exercise corresponding to personal datas, the number of consumed calories according to such quantity of exercise, the aimed number of taken calories at the appointed day and the menu of meal suited to such numbers of calories may be mentioned.

In addition, it can achieve the subject matters by changing the acting program or increasing or changing the datas in the memory unit.

What is claimed is:

1. A card type physical checker comprising:
   a case; said case having a thickness substantially thinner than its height and width;
   a rear face of said case;
   a pair of electrodes provided as said rear face for measuring inner body impedance;
   a front face of said case provided opposite said pair of electrodes, said front face having a display part; key pad means for inputting basic physiological data; and a group of function changing keys for selecting one of a plurality of desired operation modes, said selected operation mode adapted to accept data of measured body impedance from said pair of electrodes;
   a central processing means positioned within said case for processing signals inputted from said electrodes and data inputted from said key pad in accordance with said one selected operation mode for determining body fat corresponding to said inner body impedance; and
   a memory unit positioned within said case for storing data based on said signals inputted from said pair of electrodes and said data inputted from said key pad in said selected operation mode.

* * * * *